United States Patent [19]
Ogunbiyi et al.

[11] Patent Number: 4,783,488
[45] Date of Patent: Nov. 8, 1988

[54] CONTACT LENS WETTING SOLUTION

[75] Inventors: Lai Ogunbiyi, Fairport; Francis X. Smith, Walworth, both of N.Y.

[73] Assignee: Bausch & Lomb Incorporated, Rochester, N.Y.

[21] Appl. No.: 90,436

[22] Filed: Aug. 25, 1987

Related U.S. Application Data

[63] Continuation of Ser. No. 825,721, Jan. 31, 1987, abandoned.

[51] Int. Cl.$^4$ .................. A01N 37/52; A61N 31/155; B01F 17/30
[52] U.S. Cl. .................................... 514/635; 252/106; 252/173; 252/DIG. 14; 252/356; 514/774; 514/801; 514/840
[58] Field of Search .................. 252/106, 173, 174.23, 252/DIG. 14, DIG. 2, 356; 106/124, 125; 514/774, 801, 839, 840, 635

[56] References Cited

U.S. PATENT DOCUMENTS

| | | | |
|---|---|---|---|
| 2,547,653 | 4/1951 | Minnis et al. | 252/106 |
| 3,873,696 | 3/1975 | Randeri et al. | 424/153 |
| 3,954,644 | 5/1976 | Krezanoski et al. | 252/106 |
| 4,323,467 | 4/1982 | Fu | 252/106 |
| 4,444,785 | 4/1984 | Mandt et al. | 424/291 |

FOREIGN PATENT DOCUMENTS 1432345 4/1976 United Kingdom .

Primary Examiner—Prince E. Willis
Attorney, Agent, or Firm—Craig E. Larson; Christopher E. Blank; Bernard D. Bogdon

[57] ABSTRACT

An improved wetting solution for contact lenses is disclosed. The solution contains gelatin as a wetting agent in an amount less than 1% by weight of the solution so that the viscosity of the solution is substantially less than 15 CPS at 25° C. The solution may also contain a biguanide as a preservative.

2 Claims, 1 Drawing Sheet

CONTACT LENS WETTING SOLUTION

This is a continuation of co-pending application Ser. No. 825,721 filed on Jan. 31, 1987, now abandoned.

BACKGROUND OF THE INVENTION

1. Field of the Invention

This invention relates to improved wetting solution for contact lenses. In a specific aspect the novel wetting solutions of this invention have improved disinfecting and/or preserving properties.

2. Description of the Prior Art

Contact lenses in wide use fall into two categories: the hard or rigid corneal type lenses formed from materials prepared by polymerization of acrylic esters, such as polymethyl methacrylate (PMMA), and gel, hydrogel or soft type lenses made of polymerized hydrophilic or hydrophobic monomers, such as 2-hydroxyethyl methacrylate (HEMA).

Cleaning, storing and wetting solutions are required for both the hard and the soft types of contact lenses. These solutions usually contain a wetting aeent to enhance wearer's comfort in combination with a germicide or preservative, a viscosity builder and salts that adjust the tonicity of the solution to make them compatible with the osmolality of the tear fluid. U.S. Pat. No. 4,323,467 describes wetting solutions that may contain gelatin as a viscosity builder and the gelatin is used in an amount sufficient to achieve viscosity of the solution of 15–750 CPS at 25° C.

The hard acrylic type of contact lens is highly durable and, since the lenses do not absorb appreciable amounts of water, the selection of suitable disinfecting agents, cleaning agents or other lens care compounds is relatively non-critical.

However, unlike hard lenses, the soft type of contact lens and certain of the newer gas permeable hard contact lenses have a tendency to bind and concentrate significantly more fluids, environmental pollutants, water impurities, as well as antimicrobial agents found in lens care solutions. In most instances, the low levels of the ingredients in lens care solutions do not lead to eye tissue irritation when used properly. Nevertheless, because of the inherent binding action of protein deposits and soft lens materials, disinfecting agents and preservatives tend to build up on lens surfaces and become concentrated to potentially hazardous levels, such that corneal inflammation and other eye tissue irritation can result.

Previous efforts to alleviate the problem of binding and concentrating disinfectants and preservatives onto contact lens surfaces and reducing the potential for eye tissue irritation have not been totally satisfactory. For example, in spite of low toxicity levels, not all disinfectants are compatible for use with all types of contact lenses. Many hard lens disinfecting and preservative solutions contain benzalkonium chloride or chlorobutanol. Although they are effective antibacterial agents, their use can result in a loss of lens hydrophilic properties, cause solution instability or may even lack compatibility with certain types of hard lenses, e.g., high silicon content.

Other antibacterial agents were found to be more compatible with contact lenses and exhibit less binding on lens surfaces. Such agents are disclosed in U.S. Pat. Nos. 4,354,952, 4,361,548 and British Pat. No. 1,432,345. However, these compositions have exhibited serious disadvantages, and there is a need for improved disinfecting and preservative solutions which are compatible for use with most types of contact lenses while maintaining both a high level of antibacterial activity and low order of toxicity to eye tissue with little or no binding or concentrating of the disinfecting agent onto lens surfaces.

We have found that gelatin can be used in contact lens care solutions in amounts such that the viscosity of the solution is substantially lower than the viscosity of prior art contact lens care solutions and that the gelatin in our solutions is a highly effective wetting agent or demulcent. We have also found that the gelatin-containing solutions of our invention can also contain microbicidal effective amounts of certain biguanides or water-soluble salts thereof in such relatively small amounts that many of the problems of the prior art preservative and disinfectants are overcome.

SUMMARY OF THE INVENTION

In accordance with this invention, there is provided a contact lens wetting solution that contains gelatin in an amount such that the viscosity of the solution is substantially less than 15 CPS at 25° C. There is also provided a contact lens solution having a viscosity substantially less than 15 CPS at 25° that contains gelatin and a microbicidally effective amount of a biguanide or water soluble salt thereof.

DESCRIPTION OF THE PREFERRED EMBODIMENTS

Figure 1:
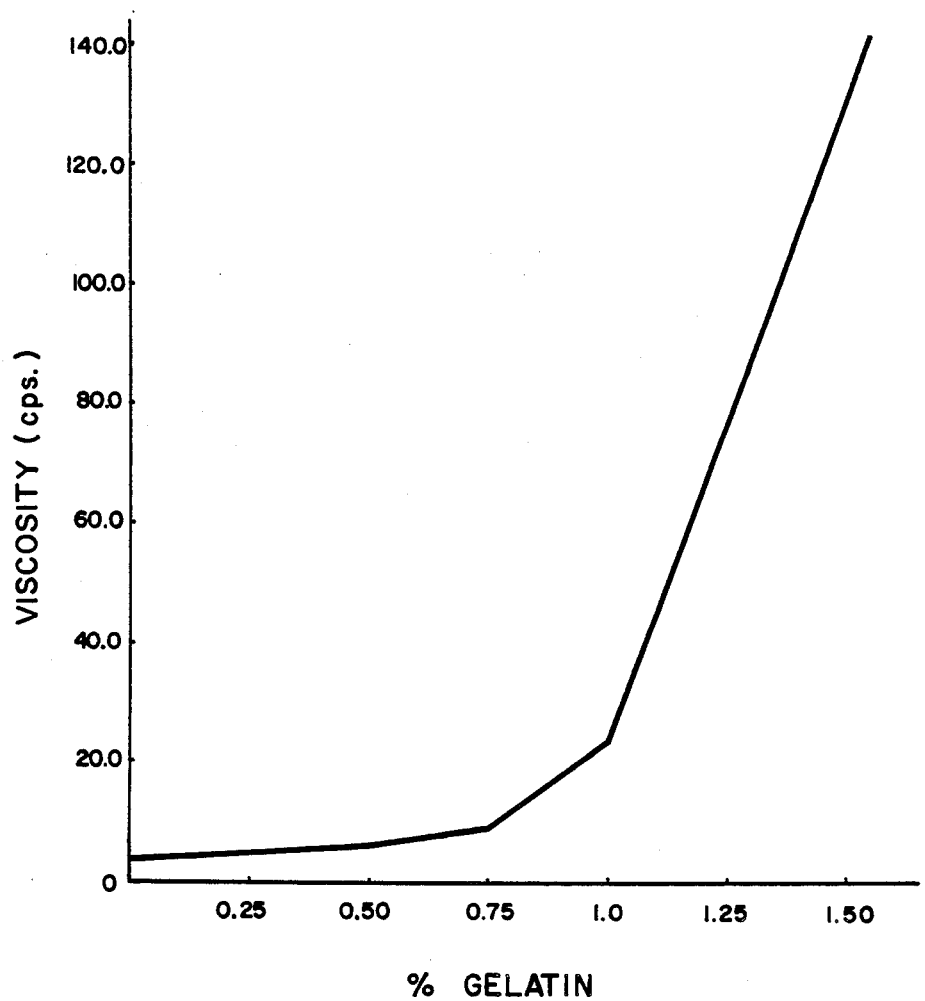

The solutions of this invention contain gelatin in an amount so that the viscosity of the solution is substantially less than 15 CPS at 25° C. The amount of gelatin that is used is less than 1% by weight of the solution and preferably not more than 0.75% by weight. Most preferably, the amount of gelatin is within the range of 0.01 to 0.75% by weight.

In addition to gelatin, the solutions of this invention may also contain other water soluble demulcents. Other demulcents are not required but among the demulcents that may be present are collagen and the water soluble cellulose derivatives, such as hydroxyethyl cellulose, methyl cellulose, carboxymethyl cellulose, hydroxypropyl methylcellulose, hydroxypropyl cellulose and the like. When other demulcents are used in addition to gelatin, the viscosity of the solution will be less than 15 CPS at 25° C. In the solutions of this invention, the gelatin improves the wettability of the solution and it increases the duration of wettability or retention time.

The solutions of this invention also contain water and one or more other components which are commonly present in contact lens care solutions, such as surfactants, germicides, buffering agents, tonicity agents and sequestering agents.

Any surfactant that is known to be useful in contact lens wetting solutions can be used in the solutions of this invention. A preferred nonionic surfactant is a poly(oxypropylene)-poly(oxyethylene) adduct of ethylenediamine having a molecular weight of 7,500 to 27,000 wherein at least 40 percent of the adduct is poly(oxyethylene). The adduct is used in an amount within the range of 0.01 to 15 percent by weight of the solution. This surfactant, which can be called a poloxamine, is markered under the trademark "Tetronic".

Any of the known buffering agents for contact lens wetting solutions can also be used. For example, any of the phosphate buffers can be used, but the borate buffers, such as boric acid, sodium borate, potassium tetraborate, potassium metaborate or mixtures thereof are preferred. Other buffers are sodium or potassium citrate, citric acid, sodium bicarbonate and various mixed phosphate buffers such as $Na_2HPO_4$, $NaH_2PO_4$ and $KH_2PO_4$. The buffers are used in an amount within the range of 0.05 to 2.5 percent by weight, preferably from 0.1 to 1.5 percent by weight.

The aqueous solutions for treating contact lenses preferably contain tonicity agents so that the osmotic pressure of the solution approximates normal lacrimal fluids which is equivalent to an 0.9 percent by weight solution of sodium chloride or a 2.5 percent by weight of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

The solutions also preferably contain a sequestering agent. Many organic acids, amines or compounds which include an acid group and an amine function are capable of acting as sequestering compounds. For example, diethylenetriamine- pentacetic acid, 1,2 diaminocylcohexane tetracetic acid, hydroxyethylaminodiacetic acid, ethylenediamine tetracetic acid and its salts, polyphosphates, citric acid and its salts, tartaric acid, and the like are useful sequestering agents. Ethylenediainetetracetic acid and its alkali metal salts are preferred. The most preferred agent is the disodium salt of ethylenediaminetetracetic acid, also known as disodium edetate.

The solutions also preferably contain a microbicidally effective amount of a germicide or disinfectant. Suitaole germicides include thimerosal, sorbic acid, 1,5 pentanedial, alkyl triethanolamines, Phenylmercuric salts, e.g. nitrate, borate, acetate, chloride and mixtures thereof. The preferred germicide is a biguanide or water soluble salt thereof having the formula $$NH_2(CH_2)_3\text{---}[(CH_2)_3\text{---}NH\text{---}\underset{\underset{NH}{\|}}{C}\text{---}NH\text{---}(CH_2)_3]_n\text{---}(CH_2)_3\text{---}NH\text{---}\underset{\underset{NH}{\|}}{C}\text{---}NH\text{---}CN$$

wherein n is from 1 to 500.

The biguanides that are used include hexamethylene biguanides, their polymers and water-soluble salts of such base compounds and polymers. The polymers have molecular weights up to 100,000 and are present in amounts from 0.000001 to 0.0003 weight percent. The solutions may also contain any of the other germicidal agents that are not incompatible with the biguanides.

The biguanide-containing solutions are effective at low concentrations against a wide spectrum of microorganisms including S. epidermidis. C. albicans. A. fumigatus, etc.

The biguanides are much more effective against the various organisms than other disinfectants such as sorbic acid particularly when used at low concentrations. The biguanides can be low molecular weight oligomers where n in the above formula averages from 4 to 7, high molecular weight long chain polymers up to 100,000 M.W., as well as individual monomers of such polymers where n is 1. The biguanides also include the water-soluble salts of the free bases, such as hydrochloride and borate salts, acetate, gluconate, sulfonate, tartrate and citrate salts. Preferably, the water-soluble salts are compounds where n has a value of 2 to 12, most preferably 3 to 8. One preferred group of water-soluble biguanides have an average molecular weight of at least 1,000 and more Particularly from 1,000 to 50,000.

It is surprising that the lower molecular weight biguanides demonstrate less binding and lower toxicity levels than other disinfectants. Also, monomers, such as hexamethylene biguanide hydrochloride, provide good bactericidal activity at low concentrations with little binding effect as does polyhexamethylene biguanide hydrochloride wherein is 4 to 7.

U.S. Pat. No. 3,428,576 describes the preparation of biguanides from a diamine and salts thereof and a diamine salt of dicyanimide. This patent teaches methods for making the hydrochloride salt of polyhexamethylenebiguanide which is commercially available from ICI Americas, Inc. under the trademark Cosmocil CQ. This biguanide is referred to hereinafter as "PHMB".

The solutions of this invention can be prepared by a variety of techniques. One method includes the preparation of a gelatin-containing solution by initially heating about 80 percent of the distilled water to be used to 80° C. With agitation the alkali metal chlorides, sequestering agents, buffering agents, surfactants, and gelatin are added in that order. Other demulcents such as hydroxypropylmethyl cellulose, hydroxyethyl cellulose, and collagen can then be added, if they are to be used. After the solution is cooled to room temperature, the PHMB is added, followed by the balance of distilled water. The solution can then be sterilized by forcing through an 0.22 micron cellulose acetate filter by means of a peristaltic pump and packaged in sterilized plastic containers.

The preservative efficacy of the solutions can be tested by exposing S. epidermis ($1 \times 10^6$ microorganisms/ml), P. aeruginosa ($1 \times 10^6$ microorganisms/ml) and E. Coli ($1 \times 10^6$ microorganisms/ml) each to 20 ml of the solution at room temperature for 14 days. Subsequently, an aliquot sample of each is placed on an agar plate and incubated for 48 hours at elevated temperatures. At the conclusion of the incubation period, the plates are examined for the development of colonies.

The following examples illustrate the invention described above.

EXAMPLE I

In this example gelatin-containing contact lens solutions were prepared according to the procedure described above. The solutions contained either PHMB or sorbic acid as a disinfectant/preservative, and the solutions were evaluated by the above test method for effectiveness against S. aureus, P. aeruginosa and E. coli organisms after 14 days. To be considered effective in this test, there must be at least 3 log ($10^3$) reduction in number of organisms for each type of organism at 14 days and at 28 days. The solutions are shown in Table I and the test results are contained in Table II. In Table I the percentages are in weight percent.

TABLE I

| Solution | HPMC % | HEC % | Gelatin % | Collagen % | Tetronic 1107% | Boric Acid % | Sodium Borate % | Sodium EDTA % | NaCl % | KCl % | PHMB ppm | Sorbic Acid % |
|---|---|---|---|---|---|---|---|---|---|---|---|---|
| 1 | 0.15 | | 0.32 | 0.10 | 0.01 | 0.85 | 0.11 | 0.022 | 0.20 | 0.30 | 1.10 | |
| 2 | | 0.20 | 0.24 | 0.10 | 0.10 | 0.85 | 0.11 | 0.011 | 0.20 | 0.30 | 0.55 | |
| 3 | 0.15 | | 0.10 | 0.10 | 0.0001 | 0.85 | 0.11 | 0.011 | 0.20 | 0.30 | 0.55 | |
| 4 | 0.15 | | 0.10 | 0.10 | | 0.85 | 0.11 | 0.011 | 0.20 | 0.30 | 0.55 | |
| 5 | | 0.40 | 0.10 | 0.20 | 0.01 | 0.85 | 0.11 | 0.011 | 0.20 | 0.30 | 0.55 | |
| 6 | 0.20 | 0.40 | 0.20 | | 0.01 | 0.85 | 0.11 | 0.022 | 0.20 | 0.30 | 1.10 | |
| 7 | 0.15 | | 0.32 | 0.10 | 0.01 | 0.85 | 0.11 | 0.022 | 0.20 | 0.30 | | 0.11 |
| 8 | | 0.20 | 0.24 | 0.10 | 0.10 | 0.85 | 0.11 | 0.011 | 0.20 | 0.30 | | 0.11 |
| 9 | 0.15 | | 0.10 | 0.10 | 0.0001 | 0.85 | 0.11 | 0.011 | 0.20 | 0.30 | | 0.11 |
| 10 | 0.15 | | 0.10 | 0.10 | | 0.85 | 0.11 | 0.011 | 0.30 | 0.30 | | 0.11 |
| 11 | | 0.40 | 0.10 | 0.20 | 0.01 | 0.85 | 0.11 | 0.011 | 0.30 | 0.30 | | 0.11 |
| 12 | 0.20 | 0.40 | 0.20 | | 0.10 | 0.85 | 0.11 | 0.022 | 0.20 | 0.30 | | 0.11 |

TABLE II

| Solution | S. aureus 14 Days | P. aeruginosa 14 Days | E. coli 14 Days |
|---|---|---|---|
| 1 | 6.6 | 6.2 | 6.0 |
| 2 | 6.6 | 6.2 | 6.0 |
| 3 | 6.6 | 6.2 | 6.0 |
| 4 | 6.6 | 6.2 | 6.0 |
| 5 | 6.6 | 3.2 | 6.0 |
| 6 | 6.6 | 6.2 | 6.0 |
| 7 | 1.5 | 6.2 | 0.9 |
| 8 | 1.6 | 6.2 | 0.9 |
| 9 | 1.9 | 6.2 | 1.0 |
| 10 | 6.6 | 6.2 | 0.8 |
| 11 | 2.0 | 6.2 | 0.8 |
| 12 | 2.8 | 6.2 | 0.8 |

EXAMPLE II

In this example, the effectiveness of polyhexamethylene biguanide hydrochloride (n=4.5 to 6.5) as a preserving agent in gelatin-containing contact lens solutions is evaluated, using an enhanced phosphate buffer system. Each preserved solution is prepared by the method described above and each is adjusted so as to be isotonic. All ingredients are by weight percent unless otherwise noted. Each solution is evaluated for effectiveness against *S. aureus, P. aeruginosa* and *E. coli* organisms after 14 and after 28 days. To be considered effective in this test, there must be at least 3 log ($10^3$) reduction in number of organisms for each type of organism at 14 days. The solutions and test results are tabulated as follows.

TABLE III
(FORMULATION)

| Ingredient | 1 | 2 | 3 | 4 | 5 | 6 | 7 |
|---|---|---|---|---|---|---|---|
| Polyvinyl Alcohol (98%) | 1.0 | 1.0 | 1.0 | 1.0 | 1.0 | 1.0 | 1.0 |
| Hydroxypropylmethyl Cellulose | 0.20 | 0.36 | 0.10 | 0.30 | 0.30 | 0.30 | 0.30 |
| Gelatin | 0.10 | 0.10 | 0.10 | 0.10 | 0.10 | 0.10 | 0.10 |
| Dibasic Phosphate | 0.45 | 0.45 | 0.45 | 0.45 | 0.45 | 0.45 | 0.45 |
| Monobasic Phosphate | 0.10 | 0.10 | 0.10 | 0.10 | 0.10 | 0.10 | 0.10 |
| Na₂ EDTA | 0.11 | 0.11 | 0.11 | 0.11 | 0.11 | 0.11 | 0.11 |
| Sodium Chlorate | 0.61 | 0.56 | 0.56 | 0.56 | 0.56 | 0.56 | 0.56 |
| PHMB | 1.1 | 1.1 | 1.1 | 1.1 | 1.1 | 1.1 | 1.1 |
| Poloxamine 1107 | — | — | — | — | — | — | 0.10 |
| Cocoamidopropyl Betaine | — | — | — | 0.10 | 0.10 | 0.10 | 0.10 |
| Water, qs to 100.0 | | | | | | | |

TABLE IV
(RESULTS)

| Solution No. | ORGANISM LOG REDUCTION[1] | | | | | |
|---|---|---|---|---|---|---|
| | S. aureus | | P. aeruginosa | | E. coli | |
| | T = 14 | T = 29 | T = 14 | T = 28 | T = 14 | T = 28 |
| 1 | 4.7 | 2.9 | 1.4 | 1.3 | 5.9 | 4.9 |
| 2 | 4.8 | 5.2 | 1.6 | 1.3 | 5.9 | 4.9 |
| 3 | 5.0 | 5.2 | 1.6 | 1.2 | 5.9 | 4.9 |
| 4 | 6.2 | 5.1 | 5.7 | 4.6 | 6.0 | 5.0 |
| 5 | 6.2 | 5.1 | 5.7 | 4.8 | 6.0 | 5.0 |
| 6 | 6.2 | 5.1 | 5.7 | 4.8 | 6.0 | 5.0 |
| 7 | 6.2 | 5.1 | 5.7 | 4.8 | 6.0 | 5.0 |

[1] 3 log reduction at 14 required for each test organism.

All of the gelatin-containing solutions of this example are effective wetting solutions for contact lenses. Since the solutions contain a phosphate buffer, an additional preservative, such as cocoamidopropyl betaine, may be needed in addition to the small amount of PHMB in order to obtain the desired organism log reduction.

EXAMPLE V

In order that gelatin will provide the desired wetting properties when used in contact lens solutions it is most desirable that the viscosity of the solution be less than 15 CPS at 25° C. In this example the gelatin concentration was varied in a solution containing the following compounds in distilled water:

| | |
|---|---|
| Sodium chloride | 0.2% |
| Potassium chloride | 0.3% |
| Edetate disodium | 0.2% |
| Sodium borate | 0.12% |
| Boric acid | 0.85% |
| Poloxamine 1107 | 0.5% |
| Hydroxypropyl Methyl cellulose | 0.1% |
| PHMB | 0.0001% |
| Collagen | 0.1% |

All percentages are in weight percent.

The gelatin concentrations were varied and the viscosity of the various solutions is shown in the following table:

| Gelatin Concentration | Viscosity (CPS) |
|---|---|
| 0.25% | 5.06 |
| 0.50% | 5.76 |
| 0.75% | 8.47 |
| 1.0% | 23.73 |
| 1.5% | 132.60 |

These data were used in the preparation of the accompanying curve shown as FIG. 1 to demonstrate the relationship between gelatin concentration and the viscosity of contact lens solutions. The viscosity was measured by using a Brookfield Viscometer (Model LVT).

We claim:

1. An aqueous contact lens wetting solution containing gelatin as a first demulcent, in an amount of at least 0.01% by weight but less than 0.75% by weight, collagen as a second demulcent, boric acid and sodium borate as buffering agents, the amount of buffering agent being within the range of 0.05 to 2.5% by weight, sodium chloride and potassium chloride as tonicity agents so that the osmotic pressure of the solution approximates normal lacrimal fluids, and a microbicidally effective amount of a biguanide as a germicide, the viscosity of the solution being less than 15 CPS at 25° C.

2. An aqueous contact lens wetting solution containing gelatin as a first demulcent, in an amount of at least 0.01% by weight but less than 0.75% by weight, collagen as a second demulcent, boric acid and sodium borate as buffering agents, the amount of buffering agent being within the range of 0.05 to 2.5% by weight, sodium chloride and potassium chloride as tonicity agents so that the osmotic pressure of the solution approximates normal lacrimal fluids, a microbicidally effective amount of the hydrochloride salt of polyhexamethylene-biguanide as a germicide, and disodium edetate as a sequestering agent, the viscosity of the solution being less than 15 CPS at 25° C.

* * * * *

UNITED STATES PATENT AND TRADEMARK OFFICE
CERTIFICATE OF CORRECTION

PATENT NO. : 4,783,488
DATED : November 8, 1988
INVENTOR(S) : Lai Ogunbiyi and Francis X. Smith It is certified that error appears in the above—identified patent and that said Letters Patent is hereby corrected as shown below:

Col. 3, line 5, change "$NaH_2HPO_4$" to "$NaH_2PO_4$".

Col. 4, line 14, insert "n" after "wherein".

Signed and Sealed this

Twenty-sixth Day of September, 1989

Attest:

DONALD J. QUIGG

Attesting Officer

Commissioner of Patents and Trademarks